US006465483B1

(12) United States Patent
Lösel et al.

(10) Patent No.: US 6,465,483 B1
(45) Date of Patent: Oct. 15, 2002

(54) ANNELATED DIHYDROPYRIDINES AND THE USE THEREOF FOR PREPARING PHARMACEUTICAL PREPARATIONS

(75) Inventors: Walter Lösel, Gau-Algesheim; Otto Roos, Schwabenheim; Dietrich Arndts, Appenheim, all of (DE)

(73) Assignee: Boehringer Ingelheim GmbH, Ingelheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/679,983

(22) Filed: Oct. 5, 2000

Related U.S. Application Data

(62) Division of application No. 09/252,373, filed on Feb. 18, 1999, now Pat. No. 6,180,645, which is a division of application No. 08/993,855, filed on Dec. 18, 1997, now Pat. No. 5,925,650, which is a continuation of application No. 08/465,637, filed on Jun. 5, 1995, now Pat. No. 5,837,712, which is a continuation of application No. 08/360,524, filed on Dec. 21, 1994, now Pat. No. 5,607,943.

(30) Foreign Application Priority Data

Dec. 21, 1993 (DE) .......................................... 43 43 641
Dec. 21, 1993 (DE) .......................................... 43 43 684

(51) Int. Cl.⁷ ............................................... A61K 31/44
(52) U.S. Cl. ................... 514/301; 514/307; 514/232.5; 514/232.8; 514/235.2
(58) Field of Search ............................. 514/307, 232.5, 514/232.8, 235.2, 301

(56) References Cited

U.S. PATENT DOCUMENTS

| 4,322,418 A | 3/1982 | Losel et al. |
| 5,837,712 A | 11/1998 | Losel et al. |
| 5,925,650 A | 7/1999 | Losel et al. |
| 6,034,094 A | 3/2000 | Losel et al. |

FOREIGN PATENT DOCUMENTS

| EP | 288048 | 4/1988 |
| EP | 358957 | 3/1990 |
| WO | WO9211010 | 7/1992 |
| WO | WO9400435 | 1/1994 |

OTHER PUBLICATIONS

Grant & Hackh's Chemical Dictionary, Fifth Edition, McGraw–Hill Book Company, New York, NY, pp. 417 (1987).
Katzung, B. G. et al, Basic & Clinical Pharmacology (Appleton & Lange, Norwalk), ed. by Katzung, B. G., pp. 171 and 178–182 (1995).
Robertson, R. M. et al, Goodman & Gilman's The Phamacological Basis of Therapeutics (McGraw–Hill, New York), ed. by Hardman, J. G., pp. 759 and 767–774 (1996).
Arndts, D. et al, Derwent World Patents Index Abstract No. 88–301110 (1988).
Burger, A., "Rational Approaches to Drug Structure", J. Chem. Ed., 33, pp. 362–372 (1956).

Primary Examiner—Dwayne C. Jones
Assistant Examiner—C. Delacroix-Muirheid
(74) Attorney, Agent, or Firm—Robert P. Raymond; Philip I. Datlow; Alan R. Stempel

(57) ABSTRACT

A compound of formula I

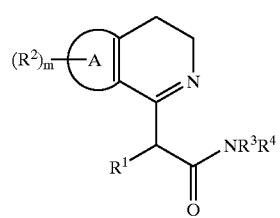

wherein
A denotes a benzo, indolo or thieno group;
$R^1$ denotes thienyl or the group

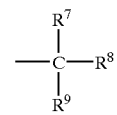

wherein
$R^7$, $R^8$ and $R^9$ independently of one another may represent methyl, ethyl, propyl, phenyl or benzyl, while not more than 2 of the substituents can simultaneously represent phenyl or benzyl;
$R^2$, m, $R^3$ and $R^4$ are defined as in the specification, as well as pharmaceutical preparations containing this compound and the new pharmaceutical uses thereof.

15 Claims, No Drawings

ANNELATED DIHYDROPYRIDINES AND THE USE THEREOF FOR PREPARING PHARMACEUTICAL PREPARATIONS

CROSS-REFERENCE TO RELATED APPLICATIONS

This application is a divisional of U.S. application Ser. No. 09/252,373, Feb. 18, 1999 now U.S. Pat. No. 6,180,645, is a divisional of U.S. application Ser. No. 08/993,855, filed Dec. 18, 1997 now U.S. Pat. No. 5,925,650, which is a continuation of U.S. application Ser. No. 08/465,637 filed Jun. 5, 1995 now U.S. Pat. No. 5,837,712, which is a continuation of U.S. application Ser. No. 08/360,524 filed Dec. 21, 1994 now U.S. Pat. No. 5,607,943.

BACKGROUND OF THE INVENTION

1. Field of the Invention

The invention relates to new annelated dihydropyridinoacetic acid derivatives, processes for preparing them and pharmaceutical compositions containing these compounds.

2. Description of the Related Art including information disclosed under 37 CFR 1.97 and 1.98.

Dihydroisoquinolines are known from EP-A 37 934. The compounds specified therein are cardiotonically active and have the effects of increasing contractility and influencing blood pressure. They have been proposed for improving blood circulation through the tissues and for improving the oxygen supply to the tissues. These possible uses are based on the vascular activity of the compounds. EP-A 251 194 and EP-A 288 048 describe how carbocyclically and heterocyclically annelated dihydropyridines have a cardioprotective or cerebroprotective activity and constitute an entirely new type of Ca-antagonistic compounds. WO 92/11010 describes the use of such compounds for cerebroprotective agents, for treating chronic inflammatory processes and for inhibiting blood clotting and blood platelet aggregation.

BRIEF SUMMARY OF THE INVENTION

The present invention relates to new carbocyclically and heterocyclically annelated dihydropyridines and the pharmaceutical use of these compounds. The new compounds have valuable therapeutically useful properties. They may be used as cardioprotective agents, as cerebroprotective agents (particularly for treating patients who have suffered a stroke or are in danger of suffering a stroke) and as agents for treating chronically inflammatory processes (e.g. bronchial asthma and arthritis). These compounds may also be used as agents with an antiproliferative effect and as agents for treating ulcerative colitis and Crohn's disease.

DETAILED DESCRIPTION OF THE INVENTION

The invention relates to compounds of general formula I

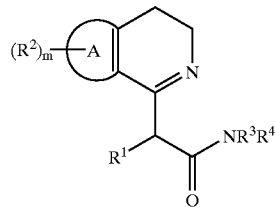

wherein

A denotes a benzo, indolo or thieno group;

wherein, if A is benzo, m is 2 or 3 (preferably 2, whilst the two $R^2$s are in positions 6 and 7) and the substituents $R^2$ independently of each other denote hydroxy, $(C_{1-4})$alkoxy, benzyloxy, halogen (F, Cl, Br, I), $(C_{1-4})$alkyl, methanesulphonyloxy or methanesulphonamido, or two adjacent substituents $R^2$ may together represent —O—$CH_2$—O— or —O—$CH_2$—$CH_2$—O—; and if A is indolo or thieno, m is zero;

$R^1$ denotes thienyl or the group

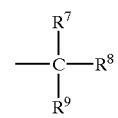

wherein $R^7$, $R^8$ and $R^9$ independently of one another may represent methyl, ethyl, propyl, phenyl or benzyl, whilst not more than 2 of the substituents can simultaneously represent phenyl or benzyl;

$R^3$ and $R^4$ independently of each other have one of the following meanings:

(a) hydrogen,
(b) branched or unbranched $C_{3-6}$-alkenyl,
(c) branched or unbranched $C_{3-6}$-alkynyl, or
(d) branched or unbranched $C_{1-12}$-alkyl, wherein the alkyl may be substituted by
hydroxy,
$(C_{1-4})$alkoxy,
di$(C_{1-4})$alkylamino,
furyl,
pyridyl,
pyrrolidinyl, N-methylpyrrolidinyl,
morpholino,
indolyl,
nitrilo,
thienyl,
adamantyl,
cyclohexyl,
phenoxy,
naphthyloxy or phenyl, [whilst this phenyl or the phenyl contained in the phenoxy group may be mono-, di- or trisubstituted by hydroxy, $(C_{1-4})$alkoxy, benzyloxy, halogen (F, Cl, Br, I), $CF_3$, $N_3$, CN, $(C_{1-4})$alkyl, adamantyl, —$SO_2NH_2$, —$NHCOCH_3$, —$NHSO_2CH_3$ or $CH_3SO_2O$— or by the bridge —O—$CH_2$—O—;] or by two unsubstituted phenyl groups;

or R³ represents hydrogen and R⁴ represents cyclohexyl, phenyl (whilst this phenyl may be mono-, di- or trisubstituted by hydroxy, (C$_{1-4}$)alkoxy, benzyloxy, halogen (F, Cl, Br, I), CF$_3$, N$_3$, (C$_{1-4}$)alkyl, adamantyl, —SO$_2$NH$_2$, —NHCOCH$_3$, —NHSO$_2$CH$_3$ or CH$_3$SO$_2$O— or by the bridge —O—CH$_2$—O—); pyridyl or N-benzylpiperidyl;

or R³ and R⁴ together with the nitrogen atom to which they are bound represent pyrrolidinyl, piperidinyl, morpholinyl, thiomorpholinyl or piperazinyl, whilst the piperazinyl ring may optionally be N-substituted by methyl, unsubstituted phenyl, mono- or di(C$_{1-4}$) alkoxyphenyl, cyano-substituted phenyl, pyrimidinyl, phenyl(C$_{1-4}$)alkyl, (C$_{1-4}$)alkylphenyl or

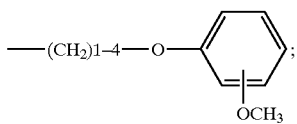

or the salts thereof with physiologically acceptable acids or complex-forming agents.

Compounds of formula I form tautomers of formula II

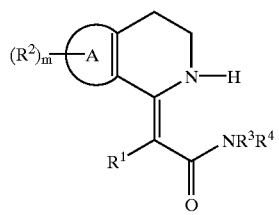

II

The tautomers can be separated by known methods, e.g. by column chromatography or selective reduction (NaBH$_4$ or catalytic reduction).

The compounds of formula II may occur in cis- and/or trans-form:

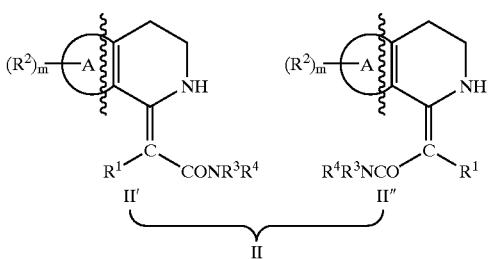

If the structure of a compound is not expressly stated, the mention of formula I should be taken as including structure II as well.

In the definitions used in the text the radicals and groups may be identical or different, i.e. if one of the above-mentioned substituents occurs several times in a particular molecule, the meaning can be selected freely within the scope of the definitions provided.

The term alkyl means C$_{1-6}$-alkyl and C$_{1-4}$-alkyl radicals which may be substituted or, as alkyl radicals, are part of a functional group such as alkoxy or alkylthio. The alkyl radicals include methyl, ethyl, n-propyl, isopropyl, n-butyl, sec.-butyl, isobutyl and tert.-butyl radicals as well as the various isomeric pentyl and hexyl radicals, such as e.g. isopentyl, neopentyl, n-pentyl and n-hexyl radicals.

The above definition thus also applies even when the alkyl radical itself is substituted and/or is itself part of an alkoxyalkyl-, alkoxycarbonyl-, alkoxy-, alkylthio-, alkylsulphonyl-, monoalkylamino-, alkylmethyl-, alkylthiomethyl- or dialkylamino- group or the alkyl radical, as a substituent, is bound to an aromatic heterocyclic or carbocyclic system.

The halogens are fluorine, chlorine, bromine and iodine, preferably fluorine, chlorine and bromine and, to a lesser extent, iodine.

C$_{3-6}$-cycloalkyl indicates cyclopropane, cyclobutane, cyclopentane and cyclohexane.

C$_{5-6}$-cycloalkenes denote e.g. cyclopentene, cyclohexene and cyclohexadiene.

C$_{3-6}$-alkynes are the isomeric hexenes, pentenes, butynes and propynes, preferably propargyl.

The C$_{3-6}$-alkenes are the isomeric hexenes, pentenes, butenes and propenes, preferably allyl.

A preferred aspect of the invention consists of compounds of general formula I wherein A denotes a benzo- or thieno group;

wherein, if A is benzo, m is 2, the R²s are in positions 6 and 7 and independently of one another represent hydroxy, (C$_{1-4}$)alkoxy, benzyloxy, halogen (F, Cl, Br, I), (C$_{1-4}$)alkyl, methanesulphonyloxy or methanesulphonamido, or two adjacent substituents R² may together represent —O—CH$_2$—O— or —O—CH$_2$—CH$_2$—O—; and if A is thieno, m is zero;

R¹ denotes thienyl or the group

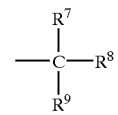

wherein

R⁷, R⁸ and R⁹ independently of one another may represent methyl, ethyl, propyl, phenyl or benzyl, whilst not more than 2 of the substituents can simultaneously represent phenyl or benzyl;

R³ and R⁴ independently of each other represent
(a) hydrogen,
(b) branched or unbranched C$_{3-6}$-alkenyl,
(c) branched or unbranched C$_{3-6}$-alkynyl, or
(d) branched or unbranched C$_{1-12}$-alkyl, wherein the alkyl may be substituted by
hydroxy,
(C$_{1-4}$)alkoxy,
di(C$_{1-4}$)alkylamino,
furyl,
pyridyl,
pyrrolidinyl, N-methylpyrrolidinyl,
morpholino,
indolyl,
nitrilo,
thienyl,
adamantyl,
cyclohexyl,
phenoxy,
naphthyloxy or phenyl, whilst this phenyl or the phenyl contained in the phenoxy group may be mono-, di- or trisubstituted by hydroxy, (C$_{1-4}$) alkoxy, benzyloxy, halogen (F, Cl, Br, I), CF$_3$, N$_3$, (C$_{1-4}$)alkyl, adamantyl, —SO$_2$NH$_2$ or —NHCOCH$_3$ or by the bridge —O—CH$_2$—O—;

or $R^3$ denotes hydrogen and $R^4$ denotes cyclohexyl, phenyl, fluorophenyl, pyridyl or N-benzylpiperidyl;

or $R^3$ and $R^4$ together with the nitrogen atom to which they are bound represent pyrrolidinyl, piperidinyl, morpholinyl, thiomorpholinyl or piperazinyl, whilst the piperazinyl ring may optionally be N-substituted by methyl, unsubstituted phenyl, mono- or di($C_{1-4}$)alkoxyphenyl, pyrimidinyl, phenyl($C_{1-4}$)alkyl or

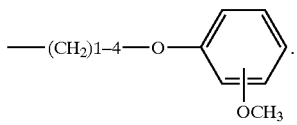

Preferably, A represents the annelated ring systems

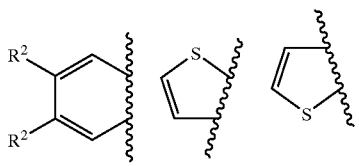

wherein $R^2$ is as hereinbefore defined.

Also preferred according to the invention are compounds I wherein A is indolo and the other substituents are as hereinbefore defined, preferably $NR^3R^4$ is either morpholinyl or in $NR^3R^4$ $R^3$ is hydrogen and $R^4$ is $C_{1-4}$-alkyl, which may be substituted as hereinbefore defined.

Of the compounds I wherein A is benzo, the preferred compounds are those wherein m is 2 and the two $R^2$s independently of each other represent methoxy, hydroxy, benzyloxy, methyl or chlorine or together represent —$OCH_2$—, whilst the two $R^2$s are in positions 6 and 7, particularly those compounds wherein $R^2$ is methoxy, hydroxy, benzyloxy or methyl, and especially those wherein both $R^2$s are the same and represent hydroxy or methoxy.

Of the compounds I, the preferred compounds are those wherein $R^1$ is tert.butyl.

Other preferred compounds of formula I are those wherein $NR^3R^4$ has one of the following meanings:

a) in $NR^3R^4$, $R^3$ is hydrogen and $R^4$ is $C_{1-6}$-alkyl;
b) in $NR^3R^4$, $R^3$ is hydrogen and $R^4$ is branched or unbranched alkynyl having 3 to 6 (preferably 3) carbon atoms
c) in $NR^3R^4$, $R^3$ is hydrogen and $R^4$ is branched or unbranched alkyl having 1 to 4 (preferably 1 to 3, especially 2) carbon atoms, the alkyl being substituted by
methoxy,
dimethylamino,
pyrrolidinyl, N-methypyrrolidinyl,
morpholino,
thienyl,
adamantyl,
pyridyl,
N-benzylpiperidyl,
cyclohexyl,
phenoxy,
naphthyloxy or 1 or 2 phenyl, whilst this phenyl (if only one phenyl group is present) or the phenyl contained in the phenoxy group may be mono-, di- or trisubstituted by methoxy, ethoxy, benzyloxy, halogen (particularly Cl, I), $CF_3$, $N_3$, methyl, tert.butyl, —$SO_2NH_2$, or by the bridge —O—$CH_2$—O—;

or $R^3$ denotes hydrogen and $R^4$ denotes cyclohexyl, phenyl, fluorophenyl, pyridyl or N-benzylpiperidyl;

d) in $NR^3R^4$, $R^3$ and $R^4$ independently of each other represent methyl, ethyl, $(CH_2)_{1-4}$-phenyl (wherein the phenyl group may be substituted like the phenyl group specified in (c)

preferably

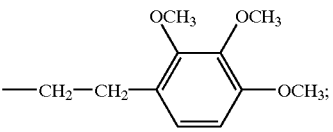

e) $R^3$ and $R^4$ together with the nitrogen atom to which they are bound denote piperidinyl, morpholinyl, thiomorpholinyl or piperazinyl, whilst the piperazinyl ring may optionally be N-substituted by methyl or benzyl;

particularly those wherein $NR^3R^4$ has one of the following meanings:

a) in $NR^3R^4$, $R^3$ is hydrogen and $R^4$ is $C_{2-6}$-alkyl;
b) in $NR^3R^4$, $R^3$ is hydrogen and $R^4$ is $CH_2CCH$;
c) in $NR^3R^4$, $R^3$ is hydrogen and $R^4$ is branched or unbranched $C_{1-4}$-alkyl, wherein the alkyl is substituted by
methoxy,
dimethylamino,
N-methypyrrolidinyl,
thienyl,
adamantyl,
phenoxy,
naphthyloxy or 1 or 2 phenyl, whilst this phenyl (if there is only one phenyl group present) or the phenyl contained in the phenoxy group may be mono-, di or trisubstituted by methoxy, ethoxy, $N_3$, methyl, tert.butyl or —$SO_2NH_2$;
d) in $NR^3R^4$, $R^3$ and $R^4$ independently of each other represent methyl, ethyl, $(CH_2)_{1-4}$-phenyl (wherein the phenyl group may be substituted by F) or particularly

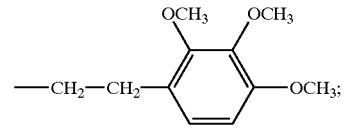

e) $R^3$ and $R^4$ together with the nitrogen atom to which they are bound are piperazinyl, N-substituted by methyl or benzyl.

Special mention should be made of compounds I wherein $NR^3R^4$ has one of the following meanings:

a) in $NR^3R^4$, $R^3$ is hydrogen and $R^4$ is ethyl, tert.butyl or $(CH_2)_1$ or $_2$—$C(CH_3)_3$;
b) $NR^3R^4$ is $NHCH_2CCH$;
c) in $NR^3R^4$, $R^3$ is hydrogen and $R^4$ is ethyl, propyl or methylpropyl which is substituted by phenyl, which may be mono-, di- or trisubstituted by methyl or methoxy or monosubstituted by tert.butyl;

d) in $NR^3R^4$, $R^3$ and $R^4$ are identical, namely

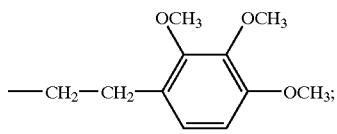

e) $NR^3R^4$ is

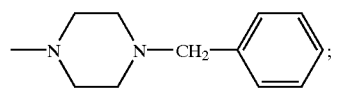

particularly those wherein $R^3$ is hydrogen or $(C_{1-4})$alkyl-phenyl and $R^4$ is $(C_{1-4})$alkyl-phenyl, whilst in these groups $C_1$-alkyl is preferably present and phenyl is mono-substituted by halogen (preferably Cl or F), $CF_3$, methoxy or ethoxy, this substituent preferably being in the o-position.

The compounds of formula I may be prepared by methods known per se, preferably analogously to the method described in German Patent Application P 37 18 570.5, EP 358 957, EP 37 934, EP 251 794 and EP 288 048.

In the presence of a condensing agent, a malonic acid diamide of general formula IV

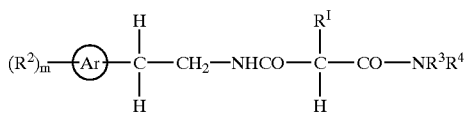

wherein $R^1$, $R^2$, $R^3$, $R^4$ and m are as hereinbefore defined and Ar represents phenyl, indolyl or 2- or 3-thienyl, may be cyclised to obtain the corresponding compounds.

Suitable condensing agents for this process are strong Lewis acids such as phosphorusoxychloride, phosphoruspentachloride, phosphorustrichloride, phosphoruspentoxide, titanium tetrachloride, boron trifluoride, tin tetrachloride, as well as inorganic acids such as polyphosphoric acid, sulphuric acid, fluorosulphonic acid and hydrofluoric acid, or mixtures of condensing agents such as a mixture of phosphorusoxychloride and phosphoruspentachloride, or a mixture of phosphoruspentoxide and $(C_{1-4})$alkylsulphonic acid, e.g. with a $P_2O_5$— content of about 10% by weight.

The cyclisation may be carried out in the presence or absence of a solvent. Any inert solvents are suitable provided that they have sufficient solubility for the reactants and a high enough boiling point, e.g. benzene, alkylbenzenes (e.g. toluene, xylene), chlorobenzenes, chloroform, acetonitrile and decaline. According to a preferred embodiment of the process the condensing agent used is phosphorusoxychloride in admixture with acetonitrile or a mixture of $(C_{1-4})$alkylsulphonic acid and phosphoruspentoxide, without the addition of solvents.

Preferably, the cyclisation is carried out with phosphorusoxychloride/acetonitrile or in difficult cases with a mixture of phosphoruspentoxide and $C_{1-4}$-alkylsulphonic acid (preferably methanesulphonic acid). The reaction can be carried out in a wide temperature range, preferably with heating to 50° C. up to the boiling point of the reaction mixture.

The necessary reaction period will be between 2 and 15 hours depending on the starting compound IV.

The 3-thiophenmalonic acid required for this preparation is commercially available. The 2-thiophenmalonic acid may be prepared by methods known per As (e.g. from 2-thiophenacetic acid using the carbonate method or from 2-thiophenbromide and diethylmalonate).

The compounds of formula I are bases and can be converted in the usual way with inorganic or organic acids and salts and complex-forming agents into any desired physiologically acceptable adducts (salts).

Acids suitable for salt formation include for example hydrochloric, hydrobromic, hydriodic, hydrofluoric, sulphuric, phosphoric, nitric, acetic, propionic, butyric, caproic, valeric, oxalic, malonic, succinic, maleic, fumaric, lactic, tartaric, citric, malic, benzoic, p-hydroxybenzoic, phthalic, cinnamic, salicylic, ascorbic, methanesulphonic acid and the like.

The compounds may be administered by oral, parenteral or topical route. The desired therapeutic dose depends on the indication and formulation used and can be determined experimentally. Suitable forms include, for example, tablets, capsules, suppositories, solutions, syrups, emulsions, aerosols or dispersible powders. Tablets may be produced, for example, by mixing the active substance or substances with known excipients, e.g. inert diluents such as calcium carbonate, calcium phosphate or lactose, disintegrants such as corn starch or alginic acid, binders such as starch or gelatine, lubricants such as magnesium stearate or talc and/or agents for obtaining delayed release, such as carboxypolymethylene, carboxymethylcellulose, cellulose acetate phthalate or polyvinylacetate. The tablets may also consist of several layers.

Coated tablets may be produced analogously by coating cores made in the same way as the tablets with substances conventionally used for tablet coatings, e.g. collidone or shellac) gum arabic, talc, titanium dioxide or sugar. In order to obtain delayed release or avoid incompatibilities the core may also consist of several layers. Similarly, the tablet coating may consist of several layers to achieve delayed release, whilst the excipients mentioned for the tablets may be used.

Syrups containing the active substances or combinations of active substances according to the invention may additionally contain a sweetener such as saccharin, cyclamate, glycerol or sugar as well as a flavour enhancer, e.g. a flavouring such as vanillin or orange extract. They may also contain suspension adjuvants or thickeners such as sodium carboxymethylcellulose, wetting agents, e.g. condensation products of fatty alcohols with ethylene oxide or preservatives such as p-hydroxybenzoates.

Injectable solutions are produced in the usual way, e.g. by adding preservatives such as p-hydroxybenzoates or stabilisers such as alkali metal salts of ethylene diamine tetraacetic acid, and are then transferred into injection vials or ampoules.

Capsules containing one or more active substances or combinations of active substances may be prepared for example by mixing the active substances with inert carriers such as lactose or sorbitol and encapsulating them in gelatine capsules.

Suitable suppositories may be produced for example by mixing with carriers provided for this purpose, such as neutral fats or polyethyleneglycol or derivatives thereof.

The compounds may be administered both enterally and parenterally. A proposed dose for oral use is 0.1 to 500 mg of active substance per dose and from 0.05 to 150 mg per dose for intravenous administration. The desired therapeutic dose depends on the indication and formulation used and can be determined experimentally.

The pharmaceutical compositions are suitable for oral or parenteral and possibly topical application. The chief formulations used are plain or coated tablets, ampoules and syrups. The single dose using these formulations is between 1.0 and 200 mg, preferably 20 to 50 mg per 75 kg of body weight. Generally, 1 to 3 single doses are required per day, depending on the gravity of the case.

The following Examples serve to illustrate the invention:

EXAMPLE 1

1. Monoethyl tert.butyl malonate

At ambient temperature over a period of 30 minutes, a solution of 7.6 g of KOH (85% strength) in 50 ml of water is added dropwise, with stirring, to a mixture of 21.6 g of diethyltert.butylmalonate, 50 ml of ethanol and 50 ml of water. After 15 hours the ethanol is distilled off in vacuo. 300 ml of $CH_2Cl_2$ are added to the residue after cooling. This is acidified with a solution of 13.6 g of $KHSO_4$ in 100 ml of $H_2O$, whilst cooling with ice, and the aqueous phase is extracted several times with $CH_2Cl_2$. The combined organic phases are washed with water, dried over $Na_2SO_4$ and concentrated by evaporation in vacuo at a bath temperature of 30° C. 15.35 g (=81.7% of theory) of monoethylester remain (bright yellow oil).

2. Monoethyl tert.butyl malonate-N-[2-(3,4-dimethoxyphenyl)ethyl]-amide

To a solution of 15.35 g of monoethyl tert.butyl malonate in 200 ml of anhydrous $CH_2Cl_2$ are stirred, at ambient temperature, 15.88 g of N,N'-carbonyldiimidazole in small batches. After 30 minutes, 14.8 g of 2-(3,4-dimethoxyphenyl)ethylamine are added. After a further 15 hours the solvent is distilled off in vacuo. The residue is mixed with 200 ml of water, acidified with 2 N HCl and extracted with ethyl acetate. The organic phase is washed with water and concentrated by evaporation after drying over $Na_2SO_4$. The residue is triturated with petroleum ether (40 to 60° C.) and brought to crystallisation.

Yield: 24.7 g (86.2% of theory); m.p. 68–70° C.

3. tert.Butylmalonic acid-mono-N-[2-(3,4-dimethoxyphenyl)-ethyl]amide 42 g of esteramide (see above) and 180 ml of 1 N NaOH are refluxed for 2 hours. After cooling and filtering, the solution is extracted with ether and acidified by the addition of 50 ml of 4 N HCl. As the solution is left to stand, crystals are precipitated out. They are suction filtered and dried at 40 to 50° C.

Yield 35.4 g (91.3% of theory). M.p. 103–104° C.

4. tert.Butylmalonic acid-N-[2-(3,4-dimethoxyphenyl)-ethyl]-N'-(3,3-diphenylpropyl)-diamide At ambient temperature, 2.1 g of N,N'-carbonyldiimidazole are added to a solution of 3.23 g of tert.butylmalonic acid monoamide (from Example 3) in 50 ml of anhydrous $CH_2Cl_2$. After 30 minutes, 2.11 g of 3,3-diphenylpropylamine are added. After 15 hours' standing at ambient temperature the solvent is distilled off. The residue is mixed with water, acidified with 2 N HCl and extracted with ethyl acetate. The organic phase is washed with water, dried over $Na_2SO_4$ and evaporated down in vacuo. The residue (4.9 g 95% of theory) is used in the cyclisation reaction without any further purification.

5. (R,S)-(3,4-Dihydro-6,7-dimethoxyisoquinolin-1-yl)-2-tert.butyl-N-(3,3-diphenylpropyl)-acetamide A mixture of 5.15 g of tert.butylmalonic acid diamide (from Example 4), 1.9 ml of $POCl_3$ and 35 ml of acetonitrile is refluxed for 2 hours. After cooling, it is poured on to ice water, made alkaline with saturated soda solution and extracted with ethyl acetate. The organic phase is washed with water, dried over $Na_2SO_4$ and evaporated down. The residue is dissolved in acetone, converted into the hydrochloride with the calculated quantity of ethereal hydrochloric acid and crystallised by trituration.

Yield: 4.45 g (83.6% of theory); m.p. 147–148° C.

EXAMPLE 2

3-Thienylmalonic acid-N-[2-(3,4-dimethoxyphenyl)ethyl]-amide

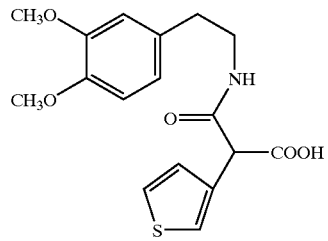

15.1 g (40 Mmol) of monoethyl-3-thienylmalonate-N-[2-(3,4-dimethoxyphenyl)ethyl]-amide are dissolved in 150 ml of methanol and 100 ml of dioxane and added dropwise to 42 ml (42 Mmol) of 1N NaOH, with stirring and cooling with ice. The mixture is stirred for a further 2 hours at ambient temperature, the organic solvents are distilled off in vacuo and the residue is distributed between water and $CH_2Cl_2$.

The aqueous phase is acidified with 10% citric acid, with cooling and stirring, and extracted with $CH_2Cl_2$. After washing with water, saturated NaCl solution and drying over $MgSO_4$, the solvent is distilled off in vacuo and a residue of 12.7 g is obtained. 11.7 g (83.7% of theory) of the title compound are obtained by recrystallisation from methylene chloride/methanol/ether.

3-Thienylmalonic acid-N-[2-(3,4-dimethoxyphenyl)ethyl]-N'-dibenzyl-diamide

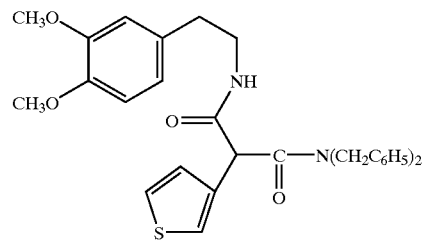

To a solution of 3.75 g (11 Mmol) of 3-thienylmalonic acid-N-[2-(3,4-dimethoxyphenyl)-ethyl]-amide in 100 ml of absolute tetrahydrofuran are added, at 5° C., with stirring, 1.78 (11 Mmol) of carbonyldiimidazole, in small batches. The reaction mixture is stirred for 30 minutes at ambient temperature and then 2.17 g (11 Mmol) of dibenzylamine are added. After 16 hours stirring at ambient temperature the mixture is evaporated down and the residue is distributed between ethyl acetate and water. The organic phase is washed successively with water, 5% $KHSO_4$ solution, saturated $NaHCO_3$ solution, water and saturated NaCl solution, dried over $MgSO_4$ and the mixture of solvents is distilled off in vacuo. The residue is recrystallised from a little ether.

Yield: 5.1 g (87.7% of theory) of the title compound are obtained.

(R,S)-(3,4-Dihydro-6,7-dimethoxyisoquinolin-1-yl)-2-(3-thienyl)-N,N-dibenzyl-acetamide

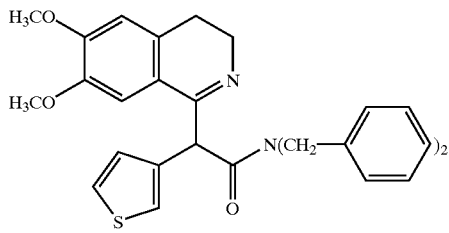

5.1 g (96 Mmol) of 3-thienylmalonic acid-N-[2-(3,4-dimethoxyphenyl)ethyl]-N'-dibenzyl-diamide are combined with 4.41 g (28.8 Mmol) of phosphorusoxychloride in 50 ml of acetonitrile (analytical grade) and the mixture is refluxed for 1 hour under an $N_2$ atmosphere. After cooling, 150 ml of ethyl acetate are added, the mixture is neutralised with saturated $NaHCO_3$ solution, washed with water and saturated NaCl solution, dried over $MgSO_4$ and the solvents are distilled off in vacuo. The residue is dissolved in 10 ml of absolute acetone, 900 mg (10 Mmol) of oxalic acid are added and the salt is precipitated in crystalline form after the addition of about 50 ml of absolute diethylether.

Yield: 4.8 g (83.3% of theory) of the title compound in the form of the oxalate; m.p.: 128–130° C.

The following Table lists examples of compounds according to the invention. These compounds may be prepared analogously to the methods described above.

TABLE 1

| X = | M.p. (° C.) | Saltform | Tautomer Structure |
|---|---|---|---|
| NH—CH₂—CH₂—(3-CF₃-C₆H₄) | 76 | Fu (1.5) | |
| NH—CH₂—CH₂—(4-CH₃-C₆H₄) | 105 | Fu | |
| NH—CH₂—CH₂—(2-Cl-C₆H₄) | 152 | Fu (1.5) | |
| NH—CH₂—CH₂—C₆H₅ | 230 | Cl | |
| NH—CH₂—CH₂—(2-CH₃-C₆H₄) | 138 | Fu (1.5) | |
| NH—CH₂—CH₂—(4-Cl-C₆H₄) | 112 | Fu | |
| NH—CH₂—CH₂—(3,4-methylenedioxyphenyl) | | | |

TABLE 1-continued
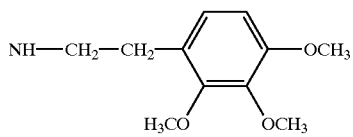
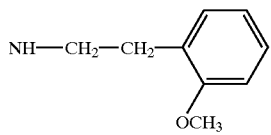     98    Fu (1.5)
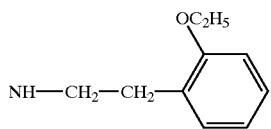
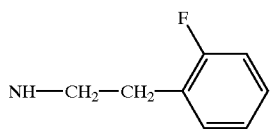     209    Cl
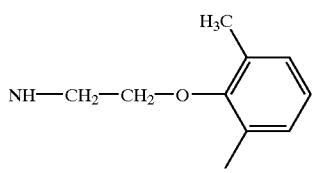
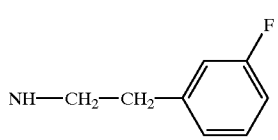     215    Cl
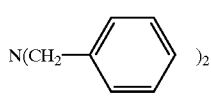
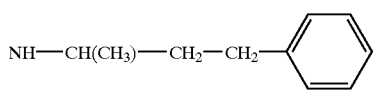
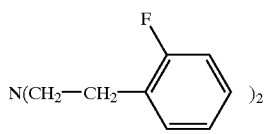
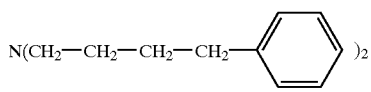
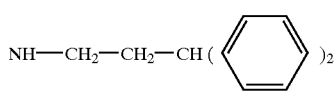     174    Fu
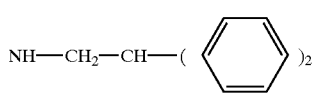     208    Fu TABLE 1-continued
| Structure | | | |
|---|---|---|---|
| 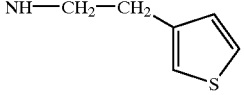 | 232 | Cl | |
| 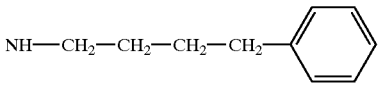 | 165 | Cl | |
| 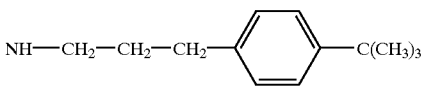 | 133 | Fu (1.5) | I |
| NH—(CH₂)₉—CH₃ | 147 | Cl | |
| 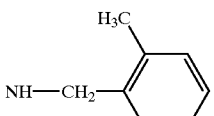 | 210 | Cl | |
| 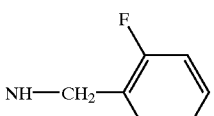 | 223 | Cl | |
| 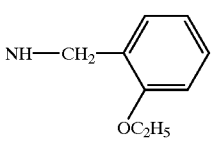 | | | |
| 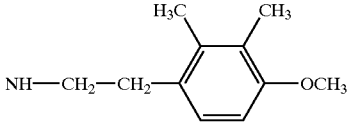 | | | |
| 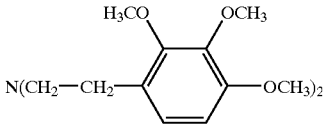 | | | |
| 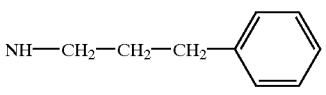 | 209 | Cl | I |
| 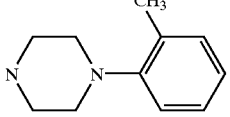 | 187 | Fu (1.5) | |
| 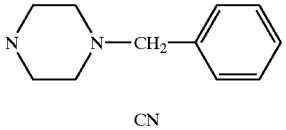 | | | |
| 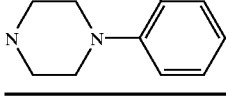 | | | |

TABLE 1-continued
| | M.p. (° C.) | Tautomer Structure | Saltform |
|---|---|---|---|
| 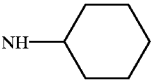 | 102 | | Fu (1.5) |
| 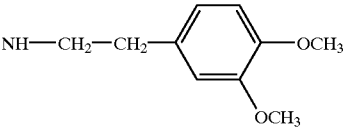 | 201 | | Fu |
| 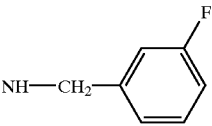 | 212 | | Cl |
| 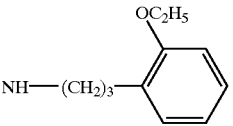 | 145 | | Fu (1.5) |
| 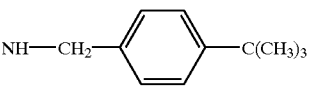 | 145 | | Fu (1.5) |
| 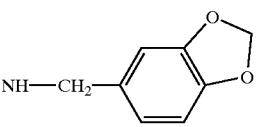 | 192 | | Fu (1.5) |
| 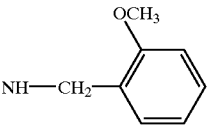 | 158 | | Fu (2) |
| 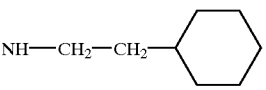 | 209 | | Cl |
| 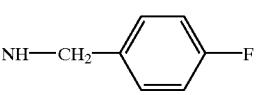 | 170 | | Cl |
| 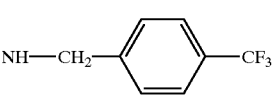 | 138 | | Cl |
| 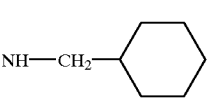 | 188 | | Cl |
| 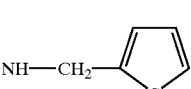 | 222 | | Cl |
| 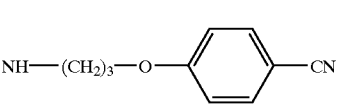 | 144 | | Fu (1.5) |

TABLE 1-continued

| Structure | M.p. | Salt-form |
|---|---|---|
| NH—CH₂—(2-OC₂H₅-C₆H₄) | 180 | Fu (1.5) |
| NH—CH₂—(2-CF₃-C₆H₄) | 210 | Fu (1.5) |
| NH—CH₂—C₆H₅ | 222 | Cl |

TABLE 2

Core structure: 6,7-dimethoxy-3,4-dihydroisoquinoline with =C(thiophen-3-yl)—C(=O)—X substituent

| X = | Salt-form | M.p. (°C.) |
|---|---|---|
| NH—CH₂—CH₂—(3-CF₃-C₆H₄) | OX | 125–135 (decomp.) |
| NH—CH₂—CH₂—(4-CH₃-C₆H₄) | BS | 161–163 |
| NH—CH₂—CH₂—(2-Cl-C₆H₄) | | |
| NH—CH₂—CH₂—C₆H₅ | | |
| NH—CH₂—CH₂—(2-CH₃-C₆H₄) | BS | 118–120 |
| NH—CH₂—CH₂—(4-Cl-C₆H₄) | | |
| NH—CH₂—CH₂—(3,4-methylenedioxyphenyl) | | |
| NH—CH₂—CH₂—(2,3,4-trimethoxyphenyl) | | |
| NH—CH₂—CH₂—(2-OCH₃-C₆H₄) | | |
| NH—CH₂—CH₂—(2-OC₂H₅-C₆H₄) | | |
| NH—CH₂—CH₂—(2-F-C₆H₄) | BS | 128–130 |

TABLE 2-continued

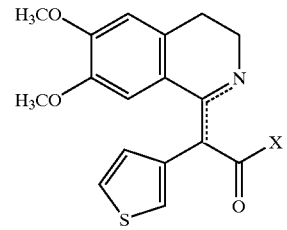

| X = | Salt-form | M.p. (° C.) |
|---|---|---|
| NH—(CH₂)₉—CH₃ | OX | 121–122 |
| NH—CH₂—[2-methylphenyl] | | |
| NH—CH₂—[2-fluorophenyl] | | |
| NH—CH₂—[2-ethoxyphenyl] | | |
| NH—CH₂—CH₂—[2,3-dimethyl-4-methoxyphenyl] | | |
| N(CH₂—CH₂—[2,3,4-trimethoxyphenyl])₂ | OX | 107–112 |
| NH—CH₂—CH₂—CH₂—C₆H₅ | | |
| NH₂ | OX | 121–140 (decomp.) |
| [2-methylphenyl-piperazine] | OX | amorph |
| [4-benzyl-piperazine] | OX | 80–100 (decomp.) |
| [2-cyanophenyl-piperazine] | | |

TABLE 2-continued

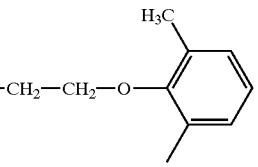

| X = | Salt-form | M.p. (° C.) |
|---|---|---|
| NH—CH₂—CH₂—O—[2,6-dimethylphenyl] | | |
| NH—CH₂—CH(C₆H₅)₂ | BS | 185–187 |
| NH—CH₂—CH₂—[3-fluorophenyl] | | |
| N(CH₂—C₆H₅)₂ | OX | 128–130 |
| NH—CH(CH₃)—CH₂—CH₂—C₆H₅ | | |
| N(CH₂—CH₂—[2-fluorophenyl])₂ | | |
| N(CH₂—CH₂—CH₂—CH₂—C₆H₅)₂ | | |
| NH—CH₂—CH₂—CH(C₆H₅)₂ | OX | 70–80 (decomp.) |
| NH—CH₂—CH₂—[3-thienyl] | BS | 165–167 |
| NH—CH₂—CH₂—CH₂—C₆H₅ | BS | 102–104 |
| NH—CH₂—CH₂—CH₂—[4-tert-butylphenyl] | OX | 124–127 |

TABLE 3

[Structure: thieno-pyridine with thiophene and C(=O)X substituent]

| X: | Saltform | M.p. (° C.) |
|---|---|---|
| NH—CH₂—CH₂—[phenyl with OCH₃, OCH₃] | BS | amorph |

OX: Oxalate
BS: free base
Decomp.: Decomposition

The present invention also relates to the use of these new compounds.

The compounds are valuable in the treatment of degenerative and necrotic diseases of the brain. It is also possible to provide preventative treatment for patients who are at risk from such diseases. The effect of the compounds is not based on an improvement in the blood flow through the tissues. The compounds are therefore suitable for a new kind of treatment of epilepsy and Alzheimer's disease and particularly for treating patients who have suffered a stroke or are at risk of suffering a stroke.

The present invention further relates to the use of the above compounds for preparing agents for the treatment of chronic inflammatory processes, ulcerative colitis and Crohn's disease and agents with an antiproliferative activity. The effect of the compounds can be explained by their inhibition of the unselective cation channels (UCC).

The pathophysiology of chronic bronchial asthma is based on inflammatory processes which are mediated by the activation of inflammatory cells. (BARNES, 1987; SEIFERT and SCHULTZ, 1991).

The receptor-regulated activation of inflammatory cells (e.g. neutrophilic granulocytes and mast cells or the permanent cell lines HL-60 cells or sensitised RBL cells, i.e. those charged with gammaglobulin E) is inhibited, irrespective of the nature of the stimulating agonists (e.g. endothelin, PAF, leukotrienes, chemotactical peptide fMLP or antigen against sensitised mast cells) by blockers of unselective cation channels (UCC) (RINK, 1990). Through these channels extracellular calcium, which is responsible for the persistence of receptor-mediated cell activations, enters the cells (PUTNEY, 1990). If this supply of calcium is interrupted this results in a blockade of the activation of inflammatory cells.

Conventional calcium antagonists of the dihydropyridine or phenylalkylamine type do not inhibit either UCCs or inflammatory processes (WELLS et al., 1986).

As a measurement of the cell activation or as a measurement of the inhibition thereof by UCC blockers, the kinetics of the cytoplasmic calcium ion concentration in fura-2-charged cells is quantified fluorometrically using the method described by GRYNKIEWICZ et al. (1985). This procedure has proved a reliable screening method, within the scope of the invention, for detecting UCC blockers.

So-called functional THAPSIGARGIN inhibition has proved suitable for the specific characterisation of blockers of the unselective cation channels. THAPSIGARGIN is a tumour promoter described by THASTRUP et al. (Proc. Natl. Acad. Sci. (USA), 87, 2466–2470, 1990) which selectively and irreversibly inhibits the $Ca^{2+}$-ATPase of intracellular $IP_3$-sensitive $Ca^{2+}$-stores. Consequently the $Ca^{2+}$-stores are rapidly depleted. As described by J. PUTNEY (Calcium, 11, 611–624, 1990) the depletion of these stores constitutes the physiological stimulation for opening up unselective cation channels in the cell membrane. The result of this is a massive influx of $Na^+$ and $Ca^{2+}$ into the cell. Because of these properties, Thapsigargin is suitable as an indirect stimulator for agonist- and $IP_3$-independent opening up of the unselective cation channels.

Within the scope of the present invention the Thapsigargin stimulation of unselective cation channels has been carried out successfully on HL 60 cells (human leukaemia cells), on hippocampal and cortical neurone cells and on RBL-cells (rat basophilic lymphoma cells) and in this way the existence of these channels in particular cell lines was demonstrated.

The cytoplasmic $Ca^{2+}$ concentration ($[Ca^{2+}]_i$) plays an important part in the cell proliferation and in tumour growth (for a summary see L. R. ZACHARSKI, Journal of Medicine 19: 145–177, 1988). In particular, the $Ca^{2+}$-influx into the cell stimulated by receptor activation with consecutive inositoltriphosphate-(IP3-)-mediation would appear to be of crucial importance for oncogenic cell proliferation (U. KIKKAWA and Y. NISHIZUKA, Ann. REV. CELL. BIOL. 2: 149–178, 1986). This mechanism also plays a part in the formation of metastases and in "Multi-Drug Resistance". (For a summary see the above-mentioned publication by L. R. ZACHARSKI, J. MED. 19: 145–177, 1980).

This hypothesis is supported by the fact that Thapsigargin, as an indirect stimulator of the unselective cation channels (UCC) not only leads to a $Ca^{2+}$-overload in the cell but is also a highly effective tumour promoter. (V. THASTRUP et al. Proceedings of the NATL. Acad. Sci: (USA) 87: 2466–2470, 1990). The blockade of the $Ca^{2+}$-influx by the UCC leads to normalisation of the intracellular Ca-ion concentration and hence to inhibition of tumour growth etc.

Conventional calcium antagonists do not inhibit these UCC. It has been found, surprisingly, that the compounds according to this invention inhibit the influx of calcium into the cell through the UCC.

As shown by S. H. MURCH et al. (Liancet 339 : 381–385, Feb. 15, 1992) endothelin I plays an important pathophysiological role in inflammatory intestinal diseases such as ulcerative colitis and Crohn's disease. Using immunohistochemical methods it has been shown that patients with Crohn's disease in the region of the submucosa and patients with ulcerative colitis in the region of the lamina propria of the epithelium of the large intestine show significantly and greatly increased concentrations of endothelin I compared with healthy normal people. It is assumed that the local secretion of endothelin causes massive vasospasms with consecutive disseminated ischaemia with microinfarcts which are regarded as the actual cause of the above diseases. The vasospasmogenic effectiveness of endothelin is explained by a $Ca^{2+}$-overload of vascular myocytes. Endothelin primarily triggers an $IP_3$-mediated intracellular release of $Ca^{2+}$ which is followed by a massive transmembranal $Ca^{2+}$-entry through dihydropyridine-insensitive channels. (M. S. Simonson et al. Clin. Invest. Med. 14: 499–507, 1991;. T. Masakai, J. Cardiovasc. Pharmacol. 13:Suppl. 5, S1–S4, 1989; D. W. Hay, R. J. Pharmacol. 100: 383–392, 1990). These channels are unselective cation channels which have also been briefly described as existing in cells of the large intestine mucosa. (Chr. Siemer and H. Gögelein, Europ. J. Physiol. 420: 319–328, 1992).

The endothelin-stimulated activation of fura-2-charged human leukaemia cells (HL 60 cells) has proved a suitable screening model for detecting functional endothelin antagonists. In conformity with G. GRYNKIEWICZ et al. (J. Biol. Chem. 260:3440–3450, 1985) the intracellular $Ca^{2+}$-concentration in the cytoplasm of HL 60 cells (suspensions) can be monitored by spectrofluorometry and quantified as a measurement of cell activation by endothelin. The stimulation was effected by adding 0.1 mM endothelin and could be inhibited in a dosage-dependent manner by means of the substances according to the invention.

The functional endothelin antagonism of the substances according to the invention is mediated through a blockade of the unselective cation channels. Consequently,detection of a functional Thapsigargin-antagonism on RBL-hm1 cells is also a suitable screening method for functional endothelin antagonists.

Carrying Out the Investigation

For screening purposes, fura-2-charged adhesive RBL-hm 1 cells are stimulated with 0.1 µM Thapsigargin in a $Ca^{2+}$-free incubation medium. After 4 minutes, extracellular $Ca^{2+}$ is restored to a concentration of 1.5 mM and, using the fura-2-fluorescence, the excessive increase in the cytoplasmic $Ca^{2+}$-concentration caused by a massive transmembranal $Ca^{2+}$-entry through unselective cation channels is recorded.

This entry is to be inhibited solely by unselective cation channel blockers in a dosage-dependent manner. Neither conventional calcium antagonists nor specific blockers of agonists which stimulate the $IP_3$-turnover are able to inhibit the transmembranal $Ca^{2+}$-entry triggered indirectly by Thapsigargin. The compounds of the present invention are distinguished by their inhibition of UCC.

The fluorometric calcium measurement in the cytoplasm of individual adhering RBL-hm1 cells is carried out analogously to the method described by KUDO and OGURA (1986) for neuronal cells. An AXIOVERT 35 fluorescence microscope made by ZEISS is used in conjunction with an imaging system made by HAMAMATSU, consisting of the ICMS-image processing system, residual light camera with control unit and image intensifier DVS 3000.

The kinetics of the cytoplasmic $Ca^{2+}$-concentration is recorded continuously as a concentration/time curve after the cell activation stimulated by Thapsigargin (0.1 µM). The curves of two activated cell cultures are compared in the presence and absence of 10 µM test substance. The area under these curves (area under the curve=AUC) is integrated and recorded as a measurement of cell activation. The inhibitory potency of the UCC-blockers tested is determined using the following equation:

$$\% H = 100 - \frac{AUC_{inh} \times 100}{AUC_{(control)}}.$$

%H=the percentage inhibition of the calcium entry through unselective cation channels which is stimulated and inhibited by 10 µM of test substance.

$AUC_{inh}$ area under the curve recorded in the presence of the stimulant plus 10 µM inhibitory test substance.

AUC control=area under the curve which is recorded only after the addition of the stimulant.

Literature Relating to the Above Explanations

BARNES P. J., I. W. RODGER and N. C. THOMSON Pathogenesis of asthma, in "ASTHMA, basic mechanisms and clinical management" ED by P. J. BARNES; ACADEMIC PRESS, LONDON, 1988

GRYNKIEWICZ G., M. POENIE and R. Y. TSIEN A new generation of $Ca^{2+}$-indicators with greatly improved fluorescence properties J. BIOL. CHEM. 26: 3440–3450, 1985

HIDE, M. and M. A. BEAVEN Calcium influx in a rat mast cell (RBL-2H3) line J. BIOL. CHEM. 266 15221–15229, 1991

KUDO, Y. and A. OGURA Glutamate-induced increase in intracellular $Ca^{2+}$-concentration in isolated hippocampal neurones BR. J. PHARMACOL. 89: 191–198; 1986

PUTNEY, J. W., jr. Capacitative Calcium entry revised CELL CALCIUM 11: 611–624, 1990

RINK, T. J. Receptor-mediated calcium entry FEBS LETT. 268: 381–385, 1990

SEIFERT, R. and G. SCHULTZ The superoxide forming NADPH oxidase of phagocytes: An enzyme system regulated by multiple mechanism REV. PHYSIOL. BIOCHEM. PHARMACOL., Vol. 117, SPRINGER VERL., 1991

WELLS, E., C. G. JACKSON, S. T. HARPER, J. MANN and R. P. EAOY Characterization of primate bronchoalveolar mast cells II, inhibition of histamine, $LTC_4$ and $PGF_{2\alpha}$ release from primate bronchoalveolar mast cells and a comparison with rat peritoneal mast cells J. IMMUNOL. 137: 3941–3945, 1986.

Results of Measurement

The percentage inhibition of UCC after Thapsigargin stimulation (0.1 µM Thapsigargin) in RBL-hm 1 cells is given. The uniform concentration of the test substances is $10^{-5}$ mol or $10^{-6}$ mol)

TABLE 4
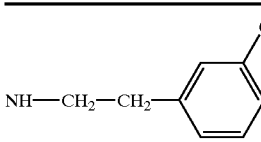
| X = | Saltform | % H (10$^{-5}$ M) | % H (10$^{-6}$ M) |
|---|---|---|---|
| 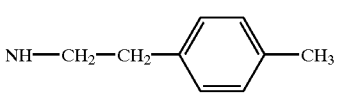 | Fu (1.5) | | 71.9 |
| 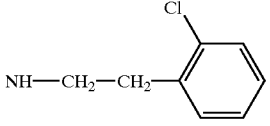 | Fu | | 57.3 |
| 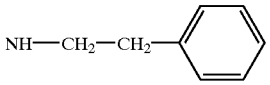 | Fu (1.5) | | 71.2 |
| 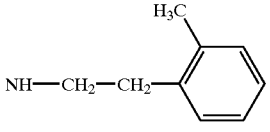 | Cl | | 66.4 |
| 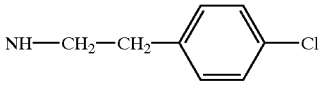 | Fu (1.5) | | 53.3 |
| 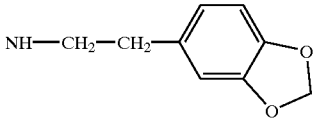 | Fu | | 70.7 |
| 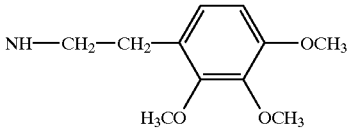 | | | |
| 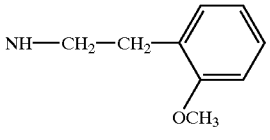 | | | |
| 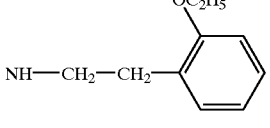 | Fu (1.5) | 60.5 | |

TABLE 4-continued
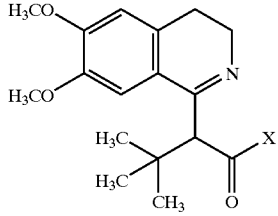
| X = | Saltform | % H ($10^{-5}$ M) | % H ($10^{-6}$ M) |
|---|---|---|---|
| 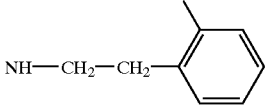 | Cl | | 64.6 |
| 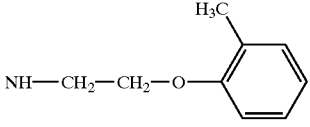 | | | |
| 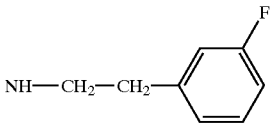 | Cl | | 70.1 |
| 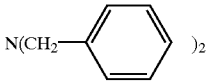 | | | |
| 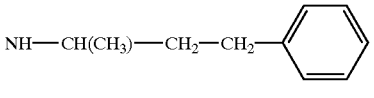 | | | |
| 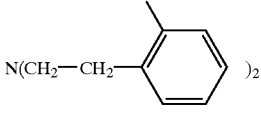 | | | |
| 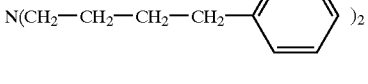 | | | |
| 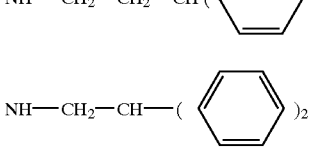 | Fu | | 77.2 |
| 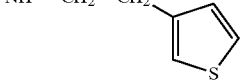 | Fu | | 75.7 |
| 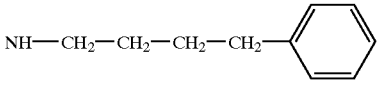 | Cl | | 24.8 |
| NH—CH$_2$—CH$_2$—CH$_2$—CH$_2$—C$_6$H$_5$ | Cl | | 64.4 |

TABLE 4-continued

[Structure: 6,7-dimethoxy-3,4-dihydroisoquinoline connected at position 1 to CH(C(CH3)3)-C(=O)-X]

| X = | Saltform | % H (10⁻⁵ M) | % H (10⁻⁶ M) |
|---|---|---|---|
| NH—CH₂—CH₂—CH₂—C₆H₄—C(CH₃)₃ (para) | Fu (1.5) | | 74.4 |
| NH—(CH₂)₉—CH₃ | Cl | | 69.7 |
| NH—CH₂—(2-CH₃-C₆H₄) | Cl | | 45.8 |
| NH—CH₂—(2-F-C₆H₄) | Cl | | 80.8 |
| NH—CH₂—(2-OC₂H₅-C₆H₄) | | | |
| NH—CH₂—CH₂—(2,3-dimethyl-4-methoxyphenyl) | | | |
| N(CH₂—CH₂—(2,3,4-trimethoxyphenyl))₂ | | | |
| NH—CH₂—CH₂—CH₂—C₆H₅ (3) | Cl | | 64.9 |
| N-piperazinyl-(2-CH₃-C₆H₄) | Fu (1.5) | 66.8 | |
| N-piperazinyl-CH₂-C₆H₅ | | | |
| N-piperazinyl-(2-CN-C₆H₄) | | | |

TABLE 4-continued
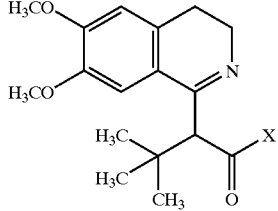
| X = | Saltform | % H ($10^{-5}$ M) | % H ($10^{-6}$ M) |
|---|---|---|---|
| 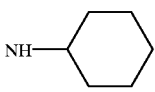 | Fu (1.5) | | 73.8 |
| 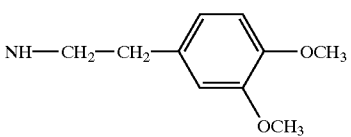 | Fu | | 29.2 |
| 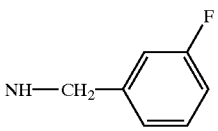 | Cl | | 72.7 |
| 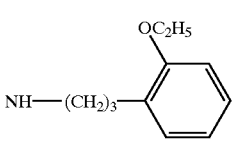 | Fu (1.5) | | 28.4 |
| 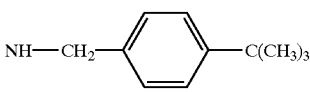 | Fu (1.5) | | 43.2 |
| 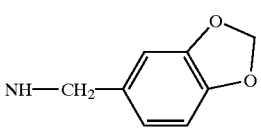 | Fu (1.5) | | 16.9 |
| 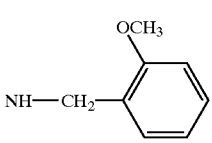 | Fu (2) | | 35.7 |
| 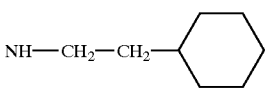 | Cl | | 53.3 |
| 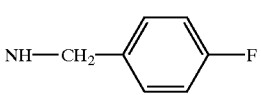 | Cl | 100.0 | 60.3 |
| 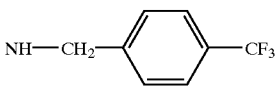 | Cl | 93.5 | 47.3 |
| 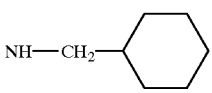 | Cl | 99.0 | 63.7 |

TABLE 4-continued
[Structure: 6,7-dimethoxy-3,4-dihydroisoquinoline with α-tert-butyl acetyl group C(=O)X]
| X = | Saltform | % H (10⁻⁵ M) | % H (10⁻⁶ M) |
|---|---|---|---|
| NH—CH₂—(2-thienyl) | Cl | 96.0 | 65.4 |
| NH—(CH₂)₃—O—C₆H₄—CN | Fu (1.5) | 91.6 | 65.7 |
| NH—CH₂—(2-OC₂H₅-C₆H₄) | Fu (1.5) | 65.8 | |
| NH—CH₂—(2-CF₃-C₆H₄) | Fu (1.5) | 51.1 | |
| NH—CH₂—C₆H₅ | Cl | 61.0 | |
TABLE 5
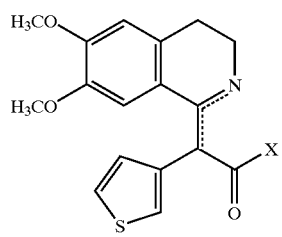
| X = | Salt-form | % H (10⁻⁵ M) |
|---|---|---|
| NH—CH₂—CH₂—(3-CF₃-C₆H₄) | OX | 20.85 |
| NH—CH₂—CH₂—(4-CH₃-C₆H₄) | BS | 59.94 |
TABLE 5-continued
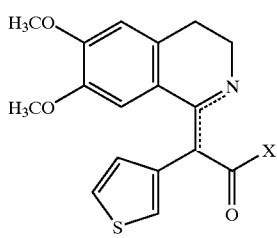
| X = | Salt-form | % H (10⁻⁵ M) |
|---|---|---|
| NH—CH₂—CH₂—(2-Cl-C₆H₄) | | |
| NH—CH₂—CH₂—C₆H₅ | | |

TABLE 5-continued

Structure: 6,7-dimethoxy-3,4-dihydroisoquinoline with =C(thiophen-3-yl)-C(=O)-X substituent at position 1

| X = | Salt-form | % H ($10^{-5}$ M) |
|---|---|---|
| NH—CH₂—CH₂—(2-methylphenyl) | BS | 37.83 |
| NH—CH₂—CH₂—(4-chlorophenyl) | | |
| NH—CH₂—CH₂—(benzo[1,3]dioxol-5-yl) | | |
| NH—CH₂—CH₂—(2,3,4-trimethoxyphenyl) | | |
| NH—CH₂—CH₂—(2-methoxyphenyl) | | |
| NH—CH₂—CH₂—(2-ethoxyphenyl) | BS | 36.41 |
| NH—CH₂—CH₂—O—(2,6-dimethylphenyl) | | |
| NH—CH₂—CH(phenyl)₂ | BS | 39.71 |
| NH—CH₂—CH₂—(3-fluorophenyl) | | |
| N(CH₂—phenyl)₂ | OX | 90.9 |
| NH—CH(CH₃)—CH₂—CH₂—phenyl | | |
| N(CH₂—CH₂—(2-fluorophenyl))₂ | | |
| N(CH₂—CH₂—CH₂—CH₂—phenyl)₂ | | |
| NH—CH₂—CH₂—CH(phenyl)₂ | OX | 22.62 |
| NH—CH₂—CH₂—(thiophen-3-yl) | BS | 14.6 |
| NH—CH₂—CH₂—CH₂—phenyl | BS | 25.76 |
| NH—CH₂—CH₂—CH₂—(4-tert-butylphenyl) | OX | 50.61 |
| NH—(CH₂)₉—CH₃ | OX | 47.09 |
| NH—CH₂—(2-methylphenyl) | | |

TABLE 5-continued

[Structure: 6,7-dimethoxy-3,4-dihydroisoquinoline with thiophene and C(=O)X substituent]

| X = | Salt-form | % H (10⁻⁵ M) |
|---|---|---|
| NH—CH₂—(2-F-phenyl) | | |
| NH—CH₂—(2-OC₂H₅-phenyl) | | |
| NH—CH₂—CH₂—(2,3-dimethyl-4-OCH₃-phenyl) | | |
| N(CH₂—CH₂—(3,4,5-trimethoxyphenyl))₂ | OX | 28.14 |
| NH—CH₂—CH₂—CH₂—phenyl | | |
| NH₂ | OX | |
| 4-(2-methylphenyl)piperazin-1-yl | OX | 6.8 |
| 4-benzylpiperazin-1-yl | OX | 52.26 |
| 4-(2-cyanophenyl)piperazin-1-yl | | |

TABLE 6

[Structure: thieno-pyridine with thiophene and C(=O)X substituent]

| Saltform | % H (10⁻⁵M) |
|---|---|

| X | Saltform | % H (10⁻⁵M) |
|---|---|---|
| NH—CH₂—CH₂—(3,4-dimethoxyphenyl) | BS | 27.01 |

The functional antiinflammatory effectiveness can be demonstrated by means of the following test:

Individual RBL-2H3-cells (a tumour cell line related to the mast cells) adhering to glass slides are used.

The cultivation and attachment of the RBL-2H3-cells are carried out by the method described by HIDE and BEAVEN (1991). In order to sensitise the adhesive RBL-2H3-cells the cells are incubated for 2 hours at ambient temperature with a 1:2000 diluted commercial gammaglobulin E-solution against a dinitrophenol-bovine serum albumin complex (DNP-BSA-antigen). The cells are then washed. By the addition of 0.1 ml of DNP-BSA-solution (10 μg/ml) there is a massive immunological cell activation which is mediated by a cytoplasmic $Ca^{2+}$-overload. The fluorometric calcium measurement in the cytoplasm of individual adhering RBL-2H3-cells is carried out analogously to the method described by KUDO and OGURA (1986) for neuronal cells, which is also explained hereinbefore in this specification.

The comparison used in these investigations is (10 μM) chromoglycate which brings about an approximately 50% inhibition of the antigen-induced cell activation.

In this test the above-mentioned compounds demonstrate %H values which are comparable with the values specified hereinbefore.

Tests on microcultures of various human tumour cell lines using the tetrazolium assay in order to determine the antiproliferative effect of the substances according to the invention surprisingly showed that the compound tested was 5 to 100 times more potent than the comparison substance Verapamil.

The antiproliferative effectiveness of the test substances was determined by means of the MTT test described by MOSMANN (J. IMMUNOL. METH. 65: 55–63, 1983), DENIZOT et al. (J. IMMUNOL. METH. 89: 271–277, 1986) and J. ELIASON et al. (INT. J. CANCER 46: 113–117, 1990). (MTT=[3-(4,5-dimethylthiazol-2-yl)2,5-diphenyl-tetrazolium bromide] produced by CHEMICON Inc. El Segundo, Calif., USA). This indicator is metabolised only by living cells with intact mitochondria into a blue formazane product. The following human tumour cell lines were used in our test; A 549 (adenocarcinoma of the lung), A 431 (epidermal carcinoma of the vulva), PC 3 (adenocarcinoma of the prostate), SK BR 3 (adenocarcinoma of the breast), HT 29 (CX1 1) (adenocarcinoma of the colon) and K 562 (chronic myeloid leukaemia cell).

The test was carried out on microtitre plates. Each well contained 100 μl of a cell suspension (0.2×10⁶ cells per ml).

The incubation medium used was RPMI 1640 with 10% heat-inactivated foetal calves' serum and 50 µg/ml of gentamycin. The cell suspensions were incubated for 0, 24, 48 or 72 hours in air with a humidity at saturation point in a $CO_2$ (5%)/air (95%) mixture at 37° C., incubated in the presence and absence of variable concentrations of antiproliferative test substances. The test substances were dissolved in DMSO (final dilution: 0.1%). Then 10 µl of MTT-solution (3 mg/ml) were added, followed after 3 hours by 100 µl of an isopropanol solution containing 0.08 N HCl. After a further hour, the light absorption at 570 nm (comparative wavelength 630 nm) was determined in a microplate reader. The light absorption is directly proportional to the number of living cells. The half-maximum inhibitory concentrations of the substances tested were 1 µg/ml.

The vasospasmolytic effectiveness of the above-mentioned functional endothelin and Thapsigargin antagonists were confirmed on an isolated blood vessel preparation: coronary perfusion was continuously quantified, on retrogressively perfused, spontaneously beating LANDENDORFF hearts taken from rats, by means of electromagnetic flow measurement (apparatus supplied by Hugo Sachs Elektronik, MARCH). This measuring apparatus could be used to record the extent, duration and pattern of vascular spasms with a high degree of accuracy. If perfusion is carried out with 100 nM endothelin concentration, the coronary perfusion flow is reduced from 11 to 5 ml/min. The restriction in perfusion can be reversed by means of the substances according to the invention. The potencies of the compounds according to the invention with regard to Thapsigargin inhibition on fura-2-charged RBL-hml-cells or the effectiveness of endothelin-inhibition on fura-2-charged HL 60 cells correlates clearly with the vasospasmolytic effectiveness of the test substances detected on the Langendorff preparation. It can be concluded from this that, underlying the vasospasmoiytic endothelin antagonism of the substances tested, there is a blockade of the unselective cation channels.

Examples of Pharmaceutical Preparations a) Coated tablets
1 tablet core contains:

| | |
|---|---|
| Active substance of general formula I | 30.0 mg |
| Lactose | 100.0 mg |
| Corn starch | 75.0 mg |
| Gelatine | 3.0 mg |
| Magnesium stearate | 2.0 mg |
| | 210.0 mg |

Preparation

The active substance mixed with lactose and corn starch is granulated with a 10% aqueous gelatine solution through a 1 mm mesh screen, dried at 40° C. and rubbed through a screen once more. The granules thus obtained are mixed with magnesium stearate and compressed. The cores produced in this way are coated in the usual manner with a coating consisting of an aqueous suspension of sugar, titanium dioxide, talc and gum arabic. The finished coated tablets are polished with beeswax.

b) Tablets

| | |
|---|---|
| Active substance of general formula I | 30.0 mg |
| Lactose | 100.0 mg |
| Corn starch | 70.0 mg |
| Soluble starch | 7.0 mg |
| Magnesium stearate | 3.0 mg |
| | 210.0 mg |

Preparation

The active substance and magnesium stearate are granulated with an aqueous solution of the soluble starch, the granules are dried and intimately mixed with lactose and corn starch. The mixture is then compressed into tablets weighing 210 mg.

c) Capsules

| | |
|---|---|
| Active substance according to formula I | 20.0 mg |
| Lactose | 230.0 mg |
| Corn starch | 40.0 mg |
| Talc | 10.0 mg |
| | 300.0 mg |

Preparation

The active substance, lactose and corn starch are first combined in a mixer and then in a grinding machine. The mixture is returned to the mixer, thoroughly combined with the talc and mechanically packed into hard gelatine capsules.

d) Tablets

| | |
|---|---|
| Active substance according to the invention | 40.0 mg |
| Lactose | 100.0 mg |
| Corn starch | 50.0 mg |
| Colloidal silica | 2.0 mg |
| Magnesium stearate | 3.0 mg |
| total | 195.0 mg |

Preparation

The active substance is mixed with some of the excipients and granulated with a solution of the soluble starch in water. After the granules have dried the remaining excipients are added and the mixture is compressed to form tablets.

e) Coated tablets

| | |
|---|---|
| Active substance according to the invention | 20.0 mg |
| Lactose | 100.0 mg |
| Corn starch | 65.0 mg |
| Colloidal silica | 2.0 mg |
| Soluble starch | 5.0 mg |
| Magnesium stearate | 3.0 mg |
| total | 195.0 mg |

Preparation

The active substance and excipients are compressed to form tablet cores as described in Example a) and these are then coated in the usual way with sugar, talc and gum arabic.

| f) | Suppositories | |
|---|---|---|
| | Active substance according to the invention | 50.0 mg |
| | Lactose | 250.0 mg |
| | Suppository mass q.s. ad | 1.7 g |

Preparation

The active substance and lactose are mixed together and the mixture is uniformly suspended in the molten suppository mass. The suspensions are poured into chilled moulds to form suppositories weighing 1.7 g.

| g) | Ampoules | |
|---|---|---|
| | Active substance according to the invention | 20.0 mg |
| | Sodium chloride | 5.0 mg |
| | Twice distilled water q.s. ad | 2.0 ml |

Preparation

The active substance and the sodium chloride are dissolved in twice distilled water and the solution is transferred under sterile conditions into ampoules.

| h) | Ampoules | |
|---|---|---|
| | Active substance according to the invention | 10.0 mg |
| | Sodium chloride | 7.0 mg |
| | Twice distilled water q.s. ad | 1.0 ml |
| i) | Drops | |
| | Active substance according to the invention | 0.70 g |
| | Methyl p-hydroxybenzoate | 0.07 g |
| | Propyl p-hydroxybenzoate | 0.03 g |
| | Demineralised water q.s. ad | 100.00 ml |

Preparation

The active substance and preservatives are dissolved in demineralised water, the solution is filtered and transferred into 100 ml vials.

What is claimed is:

1. A compound of formula I

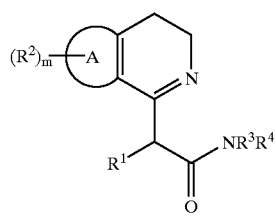

I wherein
  A is a benzo; wherein, m is 2 or 3 and the substituents $R^2$ independently of each other are hydroxy, $(C_{1-4})$alkoxy, halogen, $(C_{1-4})$alkyl, methanesulphonyloxy or methanesulphonamido, or two adjacent substituents $R^2$ may together be —O—CH$_2$—O— or —O—CH$_2$—CH$_2$—O—;
  $R^1$ is thienyl;
  $R^3$ and $R^4$ independently of each other have one of the following meanings:
    (a) hydrogen,
    (b) branched or unbranched $C_{3-6}$-alkenyl,
    (c) branched or unbranched $C_{3-6}$-alkynyl, or
    (d) branched or unbranched $C_{1-2}$-alkyl, wherein the alkyl is optionally substituted by
      hydroxy,
      $(C_{1-4})$alkoxy,
      di$(C_{1-4})$alkylamino,
    furyl,
    pyridyl,
    pyrrolidinyl, N-methylpyrrolidinyl,
    morpholino,
    indolyl,
    nitrilo,
    thienyl,
    adamantyl,
    cyclohexyl,
    phenoxy,
    naphthyloxy or phenyl, wherein this phenyl or the phenyl contained in the phenoxy group is optionally mono-, di- or trisubstituted by hydroxy, $(C_{1-4})$alkoxy, benzyloxy, halogen, $CF_3$, $N_3$, CN, $(C_{1-4})$alkyl, adamantyl, —SO$_2$NH$_2$, —NHCOCH$_3$, —NHSO$_2$CH$_3$ or CH$_3$SO$_2$O— or by the bridge —O—CH$_2$—O—; or by two unsubstituted phenyl groups;
  or $R^3$ is hydrogen and $R^4$ is cyclohexyl, phenyl wherein this phenyl is optionally mono-, di- or trisubstituted by hydroxy, $(C_{1-4})$ alkoxy, benzyloxy, halogen, $CF_3$, $N_3$, $(C_{1-4})$alkyl, adamantyl, —SO$_2$NH$_2$, —NHCOCH$_3$, —NHSO$_2$CH$_3$ or CH$_3$SO$_2$O— or by the bridge —O—CH$_2$—O—; or $R^3$ is hydrogen and $R^4$ is pyridyl or N-benzylpiperidyl;
  or $R^3$ and $R^4$ together with the nitrogen atom to which they are bound are pyrrolidinyl, piperidinyl, morpholinyl, thiomorpholinyl or piperazinyl, wherein the piperazinyl ring is optionally N-substituted by methyl, unsubstituted phenyl, mono- or di$(C_{1-4})$ alkoxyphenyl, cyano-substituted phenyl, pyrimidinyl, phenyl$(C_{1-4})$alkyl, $(C_{1-4})$alkylphenyl or

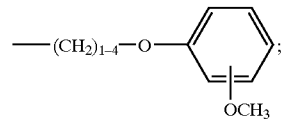

or the salts thereof with physiologically acceptable acids or complex-forming agents.

2. The compound as recited in claim 1 wherein $R^3$ and $R^4$ independently of each other are
  (a) hydrogen,
  (b) branched or unbranched $C_{3-6}$-alkenyl,
  (c) branched or unbranched $C_{3-6}$-alkynyl, or
  (d) branched or unbranched $C_{1-12}$-alkyl, wherein the alkyl is optionally substituted by
    hydroxy,
    $(C_{1-4})$alkoxy,
    di$(C_{1-4})$alkylamino,
    furyl,
    pyridyl,
    pyrrolidinyl, N-methylpyrrolidinyl,
    morpholino,
    indolyl,
    nitrilo,
    thienyl, adamantyl,
cyclohexyl,
phenoxy,
naphthyloxy or phenyl, wherein this phenyl or the phenyl contained in the phenoxy group is optionally mono-, di- or trisubstituted by hydroxy, $(C_{1-4})$ alkoxy, benzyloxy, halogen, $CF_3$, $N_3$, $(C_{1-4})$alkyl, adamantyl, $—SO_2NH_2$, $—NHCOCH_3$, $—NHSO_2CH_3$ or $CH_3SO_2O—$ or by the bridge $—O—CH_2—O—$;
or $R^3$ is hydrogen and $R^4$ is cyclohexyl, phenyl wherein this phenyl is optionally mono-, di- or trisubstituted by hydroxy, $(C_{1-4})$alkoxy, benzyloxy, halogen, $CF_3$, $N_3$, $(C_{1-4})$alkyl, adamantyl, $—SO_2NH_2$, $—NHCOCH_3$, $—NHSO_2CH_3$ or $CH_3SO_2—$, or by the bridge $—O—CH_2—O—$; or $R^3$ is hydrogen and $R^4$ is pyridyl or N-benzylpiperidyl;
or $R^3$ and $R^4$ together with the nitrogen atom to which they are bound are pyrrolidinyl, piperidinyl, morpholinyl, thiomorpholinyl, or piperazinyl, wherein the piperazinyl ring is optionally N-substituted by methyl, unsubstituted phenyl, mono- or di($C_{1-4}$)alkoxyphenyl, pyrimidinyl, phenyl ($C_{1-4}$)alkyl or

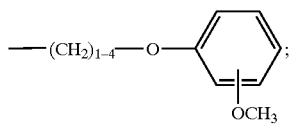

or the salts thereof with physiologically acceptable acids or complex-forming agents.

3. The compound as recited in claim 1 wherein m is 2, the two $R^2$s are in positions 6 and 7 and independently of each other are hydroxy, $(C_{1-4})$alkoxy, halogen, $(C_{1-4})$alkyl, methanesulphonyloxy or methanesulphonamido, or two adjacent substituents $R^2$ may together be $—O—CH_2—O—$ or $—O—CH_2—CH_2—O—$;

$R^3$ and $R^4$ independently of each other have one of the following meanings:
(a) hydrogen,
(b) branched or unbranched $C_{3-6}$-alkenyl,
(c) branched or unbranched $C_{3-6}$-alkynyl, or
(d) branched or unbranched $C_{1-12}$-alkyl, wherein the alkyl may be substituted by hydroxy,
   $(C_{1-4})$alkoxy,
   di($C_{1-4}$)alkylamino,
   furyl,
   pyridyl,
   pyrrolidinyl, N-methylpyrrolidinyl,
   morpholino,
   indolyl,
   nitrilo,
   thienyl,
   adamantyl,
   cyclohexyl,
   phenoxy,
   naphthyloxy or phenyl, wherein this phenyl or the phenyl contained in the phenoxy group is optionally mono-, di- or trisubstituted by hydroxy, $(C_{1-4})$alkoxy, benzyloxy, halogen, $CF_3$, $N_3$, $(C_{1-4})$alkyl, adamantyl, $—SO_2NH_2$ or $—NHCOCH_3$, or by the bridge $—O—CH_2—O—$;
or $R^3$ is hydrogen and $R^4$ is cyclohexyl, phenyl, fluorophenyl, pyridyl or N-benzylpiperidyl;
or $R^3$ and $R^4$ together with the nitrogen atom to which they are bound are pyrrolidinyl, piperidinyl, morpholinyl, thiomorpholinyl or piperazinyl, wherein the piperazinyl ring is optionally N-substituted by methyl, unsubstituted phenyl, mono- or di($C_{1-4}$) alkoxyphenyl, pyrimidinyl, phenyl($C_{1-4}$)alkyl or

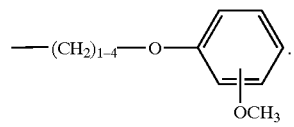

4. The compound as recited in claim 1, wherein m is 2 and the two $R^2$s independently of each other are methoxy, hydroxy, methyl or chlorine or together are $—OCH_2—$, the two $R^2$s being in positions 6 and 7.

5. The compound as recited in claim 4, wherein $R^2$ is methoxy, hydroxy or methyl.

6. The compound as recited in claim 4, wherein the group A is 6,7-dihydroxybenzo or 6,7-dimethoxybenzo.

7. The compound as recited in claim 1, wherein $R^1$ is 3-thienyl.

8. The compound as recited in claim 1, wherein $NR^3R^4$ has one of the following meanings:
a) in $NR^3R^4$, $R^3$ is hydrogen and $R^4$ is $C_{1-6}$-alkyl;
b) in $NR^3R^4$, $R^3$ is hydrogen and $R^4$ is branched or unbranched alkynyl having 3 to 6 carbon atoms,
c) in $NR^3R^4$, $R^3$ is hydrogen and $R^4$ is branched or unbranched alkyl having 1 to 4 carbon atoms, the alkyl being substituted by
   methoxy,
   dimethylamino,
   pyrrolidinyl, N-methypyrrolidinyl,
   morpholino,
   thienyl,
   adamantyl,
   pyridyl,
   N-benzylpiperidyl,
   cyclohexyl,
   phenoxy,
   naphthyloxy or 1 or 2 phenyl, wherein this phenyl, if only one phenyl group is present, or the phenyl contained in the phenoxy group are optionally mono-, di- or trisubstituted by methoxy, ethoxy, benzyloxy, halogen, $CF_3$, $N_3$, methyl, tert-butyl, $—SO_2NH_2$, or by the bridge $—O—CH_2—O—$;
or $R^3$ is hydrogen and $R^4$ is cyclohexyl, phenyl, fluorophenyl, pyridyl or N-benzylpiperidyl;
d) in $NR^3R^4$, $R^3$ and $R^4$ independently of each other are methyl, ethyl, $(CH_2)_{1-4}$-phenyl wherein the phenyl group may be substituted like the phenyl group specified in c)

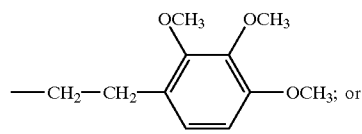

e) $R^3$ and $R^4$ together with the nitrogen atom to which they are bound are piperidinyl, morpholinyl, thiomorpholinyl or piperazinyl, the piperazinyl ring is optionally N-substituted by methyl or benzyl.

9. The compound as recited in claim 8, wherein $NR^3R^4$ has one of the following meanings:
a) in $NR^3R^4$, $R^3$ is hydrogen and $R^4$ is $C_{2-6}$-alkyl;
b) in $NR^3R^4$, $R^3$ is hydrogen and $R^4$ is $CH_2—C≡C—H$;

c) in NR³R⁴, R³ is hydrogen and R⁴ is branched or unbranched $C_{2-4}$-alkyl, wherein the alkyl is substituted by
methoxy,
dimethylamino,
N-methypyrrolidinyl,
thienyl,
adamantyl,
phenoxy,
naphtyloxy or 1 or 2 phenyl, wherein this phenyl if there is only one phenyl group present or the phenyl contained in the phenoxy group may be mono-, di- or trisubstituted by methoxy, ethoxy, N₃, methyl, tert-butyl or —SO₂NH₂;

d) in NR³R⁴, R³ and R⁴ independently of each other are methyl, ehtyl, (CH₂)₁₋₄-phenyl wherein the phenyl group may be substituted by F or

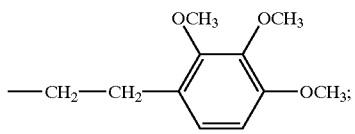

e) R³ and R⁴ together with the nitrogen atom to which they are bound are piperazinyl, N-substituted by methyl or benzyl.

10. The compound as recited in claim 8, wherein NR³R⁴ has one of the following meanings:

a) in NR³R⁴, R³ is hydrogen and R⁴ is ethyl, tert-butyl or (CH₂)₁ or 2—C(CH₃)₃;

b) NR³R⁴ is NHCH₂CCH;

c) in NR³R⁴, R³ is hydrogen and R⁴ is ethyl, propyl or methylpropyl which is substituted by phenyl, which may be mono-, di- or trisubstituted by methyl or methoxy or monosubstituted by tert-butyl; methoxy or monosubstituted by tert-butyl;

d) in NR³R⁴, R³ and R⁴ are identical, namely

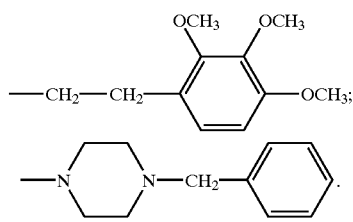

e) NR³R⁴ is

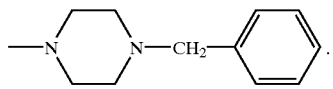

11. The compound as recited in claim 8, wherein R³ is hydrogen or $(C_{1-4})$alkyl-phenyl and R⁴ is $(C_{1-4})$alkyl-phenyl, the phenyl is mono-substituted by Cl or F, CF₃, methoxy or ethoxy, this substituent being in the o-position.

12. The compound as recited in claim 1, wherein R³ is hydrogen and R⁴ is a) $(C_{1-3})$alkyl which is substituted by phenyl, which may be substituted by CF₃, Cl, F, tert-butyl or CH₃; or b) 2,2-diphenylethyl or 3,3-diphenylpropyl; or c) cyclohexyl.

13. A pharmaceutical composition comprising a therapeutically effective amount of compound according to claim 1 and a pharmaceutical acceptable carrier.

14. A method for providing protection against stroke in a warm-blooded animal which comprises administering to said animal a therapeutically effective amount of a pharmaceutical composition according to claim 13.

15. A method for providing protection against stroke in a warm-blooded animal which comprises administering to said animal a therapeutically effective amount of a compound according to claim 1.

* * * * *